United States Patent
Sekhar

[11] B 4,033,816
[45] July 5, 1977

[54] PROCESS FOR INHIBITING PLATELET AGGREGATION

[75] Inventor: Neel C. Sekhar, Portage, Mich.

[73] Assignee: The Upjohn Company, Kalamazoo, Mich.

[22] Filed: Oct. 15, 1974

[21] Appl. No.: 514,839

[44] Published under the second Trial Voluntary Protest Program on March 2, 1976 as document No. B 514,839.

Related U.S. Application Data

[63] Continuation of Ser. No. 370,990, June 18, 1973, abandoned, which is a continuation-in-part of Ser. No. 276,714, July 3, 1972, abandoned.

[52] U.S. Cl. .............................................. 195/1.8
[51] Int. Cl.² ........................ C12B 3/00; C12B 9/00
[58] Field of Search ................................... 195/1.8

[56] References Cited

UNITED STATES PATENTS

| | | | |
|---|---|---|---|
| 3,663,584 | 5/1972 | Alvarez | 260/429.9 |
| 3,663,713 | 5/1972 | Fried et al. | 424/333 |
| 3,686,183 | 8/1972 | Dysen | 260/284 |
| 3,686,238 | 8/1972 | Zaffaroni | 260/399 |

FOREIGN PATENTS OR APPLICATIONS

| | | | |
|---|---|---|---|
| 1,211,134 | 11/1970 | United Kingdom | 30/341 |

OTHER PUBLICATIONS

O'Brien et al, The Lancet 1, pp. 894–895 (1968).
Fleming et al, Arch. Int. Pharmacodyn., 186, pp. 120–8 (1970).

*Primary Examiner*—Jerome D. Goldberg
*Attorney, Agent, or Firm*—John J. Killinger; Roman Saliwanchik

[57] ABSTRACT

A process for inhibiting platelet aggregation by the addition of a member selected from the group consisting of a compound of the formula:

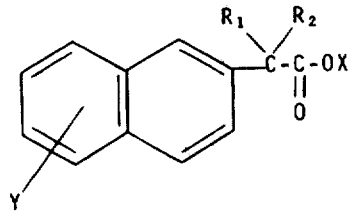

wherein Y is lower alkyl of 1 to 8 carbon atoms, cyclopropyl, ethinyl, —$CF_3$, —F, —Cl, —$OCH_3$, —$OCH_2OCH_3$, —$SCH_3$, —$SCHF_2$, —$SCH_2OCH_3$, acetyl; $R_1$ and $R_2$ are H, $CH_3$, $CHF_2$, or taken together are =$CH_2$ or =$CF_2$; and X is hydrogen, lower alkyl of 1 to 8 carbon atoms or a pharmacologically acceptable cation, to in vivo and in vitro platelet systems. In vitro systems include whole blood as kept in blood banks, whole blood as used in heart-lung machines, and platelet rich concentrates. In vivo systems include human or animal bodies. The process provides a means for treating hemorrhage due to thrombocytopenia which in turn is caused by irradiation, cancer chemotherapy, or immunosuppressants as well as hemophilia due to cogenital defects.

3 Claims, No Drawings

PROCESS FOR INHIBITING PLATELET AGGREGATION

CROSS REFERENCE TO RELATED APPLICATIONS

This application is a continuation of application Ser. No. 370,990, filed June 18, 1973, now abandoned, which in turn is a continuation-in-part of application Ser. No. 276,714, filed July 31, 1972, now abandoned.

BRIEF DESCRIPTION OF THE INVENTION

This invention relates to the prevention of platelet aggregation or thrombus formation by the addition of a compound of the Formula I to the plasma surrounding the platelets.

DETAILED DESCRIPTION OF THE INVENTION

The compounds of the Formula I are old compounds known in the art. The compounds are depicted in the protonated or acid form, however, for the purposes of the instant invention the proton can be replaced by any pharmacologically acceptable cation.

For in vivo applications the compositions of the present invention are presented for administration to humans and animals in unit dosage forms, such as tablets, capsules, pills, powders, granules, sterile parenteral solutions or suspensions, and oral solutions or suspensions, and oil-in-water and water-in-oil emulsions containing suitable quantities of the compound of Formula I.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For in vitro applications, aqueous solutions are prepared by dissolving a compound of the Formula I in water and adding salt to provide an isotonic solution and buffering to a pH compatible with blood.

Advantageously the composition prepared for parenteral administration can be used when prepared omitting the local anesthetic.

The dosage for humans and animals depends on the blood volume and condition of the subject. A dosage schedule of from about 0.1 to about 100 mg. per dose administered 1 to 3 times daily is effective for reducing platelet aggregation in the subject. Expressed in terms of weight, the dose can be from 0.001 to 1.5 mg./kg./day.

For in vitro, dosage is from 0.01 to 50 micrograms/ml. of whole blood.

The compounds of the Formula I having an asymetric carbon atom exists as optical isomers.

The compounds of the Formula I are depicted in the protonated or acid form. However, for the purposes of the instant invention, the proton can be replaced by any pharmacologically acceptable anion. These salts can be prepared in a manner analogous to the method disclosed in Netherlands Pat. No. 66 08098 (Derwent No. 24299) and can be for example those of alkali metals and alkaline earth bases, such as sodium, potassium, calcium, and magnesium; those of ammonia or a basic amine such as mono-, di-, and triethylamines, benzylamine, heterocyclic amines such as piperidine and morpholine and amines containing water-solubilizing or hydrophilic groups such as triethanolamine and phenylmonoethanolamine such as are disclosed in U.S. Pat. No. 3,296,091. Carboxylate esters such as methyl, ethyl, cyclohexyl and the like having no more than 8 carbon atoms are formed by the usual method e.g., reaction with diazomethane or similar diazohydrocarbons as in U.S. Pat. No. 3,296,091.

The addition of compounds of the Formula I to whole blood provide in vitro applications of the invention such as in the storage of whole blood in blood banks, and whole blood to be used in heart-lung machines. Additionally, whole blood containing a compound of the Formula I can be circulated through organs, e.g., heart and kidneys, which have been removed from a cadaver and prior to transplant.

The compounds of the Formula I can also be used for the preparation of stable platelet-rich plasma concentrates in the same manner as the prostaglandins as disclosed in U.S. Pat. No. 3,629,071 and Science, Vol. 175, pp. 536–542 (Feb. 4, 1972).

In vivo applications are the administration to humans and animals to prevent clot formation in situations such as following surgery to prevent postoperative thrombosis; in geriatric patients to prevent transient cerebral ischemic attacks; and long-term prophylaxis following myocardial infarcts and strokes.

In general a compound of the Formula I is usefully administered prophylactically to humans having a platelet adhesiveness value in excess of 25% [Bygdeman et al., J. Atheroscler. Res., 10, 33–39 (1969)].

EXAMPLE 1

A lot of 10,000 tablets, each containing 0.1 mg. of 2-(6-methoxy-2-naphthyl)propionic acid is prepared from the following types and amounts of ingredients:

| | |
|---|---|
| 2-(6-methoxy-2-naphthyl)propionic acid | 1 gm. |
| Dicalcium phosphate | 1,500 gm. |
| Methylcellulose, U.S.P. (15 cps.) | 60 gm. |
| Talc | 150 gm. |
| Corn starch | 200 gm. |
| Calcium stearate | 12 gm. |

The dicalcium phosphate and the active ingredient are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing thrombus formation at a dose of 1 tablet every four hours following surgery.

EXAMPLE 2

One thousand two-piece hard gelatin capsules, each containing 100 mg. of 2-(6-methoxy-2-naphthyl)propionic acid are prepared from the following types and amounts of ingredients:

| | |
|---|---|
| 2-(6-methoxy-2-naphthyl)propionic acid | 100 gm. |
| Talc | 100 gm. |
| Magnesium stearate | 10 gm. |

The ingredients are mixed well and filled into capsules of the proper size.

Capsules so prepared are useful in preventing further coronary infarcts at a dose of 1 capsule daily to a patient recovering from a coronary infarct.

EXAMPLE 3

One thousand tablets, each containing 100 mg. of 2-(6-methoxy-2-naphthyl)propionic acid are made from the following types and amounts of ingredients:

| | |
|---|---|
| 2-(6-methoxy-2-naphthyl)propionic acid | 100 gm. |
| Microcrystalline cellulose NF | 120 gm. |
| Starch | 16 gm. |
| Magnesium stearate powder | 4 gm. |

The ingredients are screened and blended together and pressed into 240 mg. tablets.

The tablets are useful to protect against transient cerebral ischemic attacks at a dose of 1 tablet daily.

EXAMPLE 4

A sterile preparation suitable for intramuscular injection and containing 1 mg. of 2-(6-methoxy-2-naphthyl)propionic acid in each milliliter is prepared from the following ingredients:

| | |
|---|---|
| 2-(6-methoxy-2-naphthyl)propionic acid | 1 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected for prophylactic treatment prior to surgery.

EXAMPLE 5—Aqueous Solution

Six hundred ml. of an aqueous solution containing 0.1 mg. of the tris(hydroxymethyl)aminomethane (THAM) salt of 2-(6-methoxy-2-naphthyl)propionic acid per ml. is prepared as follows:

| | |
|---|---|
| Tris(hydroxymethyl)aminomethane salt of 2-(6-methoxy-2-naphthyl)propionic acid | 60 mg. |
| Sodium chloride | 5,400 mg. |
| Water for injection q.s. | 600 ml. |

The THAM salt and sodium chloride are dissolved in sufficient water to make 600 ml. of sterile filtered.

The solution is added to whole blood 16.0 ml./liter for use in a heart-lung machine.

I claim:

1. A process for inhibiting platelet aggregation in vitro comprising the addition of an effective amount for inhibiting platelet aggregation of a compound of the formula:

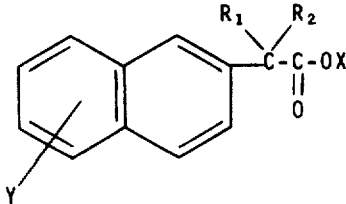

wherein Y is lower alkyl of 1 to 8 carbon atoms, cyclopropyl, ethinyl, —CF$_3$, —F, —Cl, —OCH$_3$, —OCH$_2$OCH$_3$, —SCH$_3$, —SCHF$_2$, —SCH$_2$OCH$_3$, acetyl; R$_1$ and R$_2$ are H, CH$_3$, CHF$_2$, or taken together are =CH$_2$ or =CF$_2$; and X is hydrogen, or a pharmacologically acceptable cation, to whole blood or platelet-rich concentrates.

2. The process of claim 1 wherein the amount of the compound added is from about 0.01 to 50 micrograms per ml. of whole blood.

3. The process of claim 1 wherein the compound added is 2-(6-methoxy-2-naphthyl)propionic acid.

* * * * *